(12) United States Patent
Phillips

(10) Patent No.: US 8,697,139 B2
(45) Date of Patent: Apr. 15, 2014

(54) METHOD OF INTERVERTEBRAL DISC TREATMENT USING ARTICULAR CHONDROCYTE CELLS

(75) Inventor: Frank Martin Phillips, Northbrook, IL (US)

(73) Assignee: Frank M. Phillips, Northbrook, IL (US)

( * ) Notice: Subject to any disclaimer, the term of this patent is extended or adjusted under 35 U.S.C. 154(b) by 1564 days.

(21) Appl. No.: 10/946,299

(22) Filed: Sep. 21, 2004

(65) Prior Publication Data

US 2006/0062767 A1    Mar. 23, 2006

(51) Int. Cl.
*A61K 35/32* (2006.01)
*A61K 38/18* (2006.01)
*A61P 19/00* (2006.01)
*C12N 5/077* (2010.01)

(52) U.S. Cl.
USPC .......... 424/572; 514/8.8; 514/17.1; 435/325; 435/366; 435/378; 435/384

(58) Field of Classification Search
None
See application file for complete search history.

(56) References Cited

U.S. PATENT DOCUMENTS

| | | |
|---|---|---|
| 4,642,120 A | 2/1987 | Nevo et al. |
| 4,746,654 A | 5/1988 | Breliere et al. |
| 4,846,835 A | 7/1989 | Grande |
| 4,876,248 A | 10/1989 | Breliere et al. |
| 4,904,259 A | 2/1990 | Itay |
| 4,935,233 A | 6/1990 | Bell et al. |
| 4,955,378 A | 9/1990 | Grasso |
| 5,053,050 A | 10/1991 | Itay |
| 5,053,332 A | 10/1991 | Cook et al. |
| 5,071,956 A | 12/1991 | Wautier |
| 5,105,804 A | 4/1992 | Van Nostrand |
| 5,108,438 A | 4/1992 | Stone |
| 5,114,711 A | 5/1992 | Bell et al. |
| 5,258,018 A | 11/1993 | Van Nostrand |
| 5,258,043 A | 11/1993 | Stone |
| 5,270,303 A | 12/1993 | Suzuki et al. |
| 5,284,830 A | 2/1994 | Smith et al. |
| 5,294,446 A | 3/1994 | Schlameus et al. |
| 5,374,550 A | 12/1994 | Smith et al. |
| 5,374,620 A | 12/1994 | Clark et al. |
| 5,391,203 A | 2/1995 | Bartlett et al. |
| 5,393,739 A | 2/1995 | Bentz et al. |
| 5,409,896 A | 4/1995 | Ammann et al. |
| 5,422,261 A | 6/1995 | Lee et al. |
| 5,423,817 A | 6/1995 | Lin |
| 5,424,208 A | 6/1995 | Lee et al. |
| 5,444,157 A | 8/1995 | Suzuki et al. |
| 5,489,742 A | 2/1996 | Hammer et al. |
| 5,521,291 A | 5/1996 | Curiel et al. |
| 5,547,932 A | 8/1996 | Curiel et al. |
| 5,577,995 A | 11/1996 | Walker et al. |
| 5,591,740 A | 1/1997 | Chipman et al. |
| 5,597,802 A | 1/1997 | Clark et al. |
| 5,604,204 A | 2/1997 | Ammann et al. |
| 5,607,920 A | 3/1997 | Kato et al. |
| 5,610,148 A | 3/1997 | Brown |
| 5,614,496 A | 3/1997 | Dunstan et al. |
| 5,620,867 A | 4/1997 | Kiefer et al. |
| 5,629,287 A | 5/1997 | Brown et al. |
| 5,646,316 A | 7/1997 | Jacobson et al. |
| 5,655,546 A | 8/1997 | Halpern |
| 5,656,450 A | 8/1997 | Boyan et al. |
| 5,656,598 A | 8/1997 | Dunstan et al. |
| 5,661,127 A | 8/1997 | Bhatnagar et al. |
| 5,670,538 A | 9/1997 | Franchimont et al. |
| 5,681,814 A | 10/1997 | Clark et al. |
| 5,700,774 A | 12/1997 | Hattersley et al. |
| 5,713,959 A | 2/1998 | Bartlett et al. |
| 5,719,125 A | 2/1998 | Suzuki et al. |
| 5,723,331 A | 3/1998 | Tubo et al. |
| 5,741,685 A | 4/1998 | Vacanti |
| 5,759,836 A | 6/1998 | Amin et al. |
| 5,773,563 A | 6/1998 | Shalaby |
| 5,780,436 A | 7/1998 | Bhatnagar et al. |
| 5,786,217 A | 7/1998 | Tubo et al. |
| 5,798,116 A | 8/1998 | Brown |
| 5,834,188 A | 11/1998 | Harada et al. |
| 5,836,905 A | 11/1998 | Lemelson et al. |
| 5,837,258 A | 11/1998 | Grotendorst |
| 5,846,931 A | 12/1998 | Hattersley et al. |
| 5,854,207 A | 12/1998 | Lee et al. |
| 5,855,608 A | 1/1999 | Brekke et al. |
| 5,866,165 A | 2/1999 | Liu et al. |
| 5,874,562 A | 2/1999 | Quertermous et al. |
| 5,876,452 A | 3/1999 | Athanasiou et al. |
| 5,877,281 A | 3/1999 | Quertermous et al. |
| 5,899,939 A | 5/1999 | Boyce et al. |

(Continued)

FOREIGN PATENT DOCUMENTS

| | | |
|---|---|---|
| EP | 955961 | 3/2004 |
| EP | 1437105 | 4/2004 |

(Continued)

OTHER PUBLICATIONS

Gooch et al., Tissue Eng., 2002, 8(4):591-601(abstract).*

(Continued)

*Primary Examiner* — Xiaozhen Xie
(74) *Attorney, Agent, or Firm* — Gregory B. Gulliver; The Eclipse Group LLP

(57) ABSTRACT

Harvesting articular chondrocyte cells from a non-critical location of a patient and growing additional cells for transplantation into a damaged or diseased disc of the patient.

7 Claims, 1 Drawing Sheet

(56) References Cited

U.S. PATENT DOCUMENTS

| | | |
|---|---|---|
| 5,902,741 A | 5/1999 | Purichio et al. |
| 5,902,785 A | 5/1999 | Hattersley et al. |
| 5,904,717 A | 5/1999 | Brekke et al. |
| 5,908,784 A | 6/1999 | Johnstone et al. |
| 5,916,585 A | 6/1999 | Cook et al. |
| 5,916,870 A | 6/1999 | Lee et al. |
| 5,919,702 A | 7/1999 | Purchio et al. |
| 5,922,859 A | 7/1999 | Birnstiel et al. |
| 5,932,611 A | 8/1999 | Wuthier et al. |
| 5,932,716 A | 8/1999 | Sampath |
| 5,942,534 A | 8/1999 | Trauner et al. |
| 5,948,428 A | 9/1999 | Lee et al. |
| 5,958,444 A | 9/1999 | Wallace et al. |
| 5,962,325 A | 10/1999 | Naughton et al. |
| 5,964,745 A | 10/1999 | Lyles et al. |
| 5,964,807 A | 10/1999 | Gan et al. |
| 5,972,385 A | 10/1999 | Liu et al. |
| 5,972,880 A | 10/1999 | Pelletier et al. |
| 5,980,504 A | 11/1999 | Sharkey et al. |
| 5,981,273 A | 11/1999 | Curiel et al. |
| 5,981,825 A | 11/1999 | Brekke |
| 5,986,080 A | 11/1999 | Masuda et al. |
| 5,994,109 A | 11/1999 | Woo et al. |
| 6,001,352 A | 12/1999 | Boyan et al. |
| 6,005,161 A | 12/1999 | Brekke et al. |
| 6,007,570 A | 12/1999 | Sharkey et al. |
| 6,008,013 A | 12/1999 | Reynolds |
| 6,013,853 A | 1/2000 | Athanasiou et al. |
| 6,022,735 A | 2/2000 | Curiel et al. |
| 6,024,734 A | 2/2000 | Brewitt |
| 6,027,744 A | 2/2000 | Vacanti et al. |
| 6,033,884 A | 3/2000 | Woo et al. |
| 6,048,964 A | 4/2000 | Lee et al. |
| 6,060,053 A | 5/2000 | Atala |
| 6,066,658 A | 5/2000 | Yasuma et al. |
| 6,073,051 A | 6/2000 | Sharkey et al. |
| 6,077,987 A | 6/2000 | Breitbart et al. |
| 6,077,989 A | 6/2000 | Kandel et al. |
| 6,080,579 A | 6/2000 | Hanley et al. |
| 6,083,690 A | 7/2000 | Harris et al. |
| 6,086,151 A | 7/2000 | Vanharanta |
| 6,086,863 A | 7/2000 | Ritter et al. |
| 6,090,544 A | 7/2000 | Harada et al. |
| 6,095,149 A | 8/2000 | Ashley et al. |
| 6,099,514 A | 8/2000 | Sharkey et al. |
| 6,103,491 A | 8/2000 | Sampath |
| 6,103,528 A | 8/2000 | An et al. |
| 6,110,460 A | 8/2000 | Sampath |
| 6,122,549 A | 9/2000 | Sharkey et al. |
| 6,126,682 A | 10/2000 | Sharkey et al. |
| 6,132,468 A | 10/2000 | Mansmann |
| 6,132,976 A | 10/2000 | Poole et al. |
| 6,133,230 A | 10/2000 | Anastassiades |
| 6,140,452 A | 10/2000 | Felt et al. |
| 6,150,163 A | 11/2000 | McPherson et al. |
| 6,150,168 A | 11/2000 | Woo et al. |
| 6,153,409 A | 11/2000 | Bentley et al. |
| 6,156,304 A | 12/2000 | Glorioso et al. |
| 6,171,610 B1 | 1/2001 | Vacanti et al. |
| 6,177,406 B1 | 1/2001 | Wang et al. |
| 6,177,554 B1 | 1/2001 | Woo et al. |
| 6,179,871 B1 | 1/2001 | Halpern |
| 6,183,737 B1 | 2/2001 | Zaleske et al. |
| 6,184,037 B1 | 2/2001 | Rolland et al. |
| 6,187,907 B1 | 2/2001 | Chen et al. |
| 6,197,061 B1 | 3/2001 | Masuda et al. |
| 6,197,320 B1 | 3/2001 | Shalaby |
| 6,197,586 B1 | 3/2001 | Bhatnagar et al. |
| 6,204,240 B1 | 3/2001 | Gluckman et al. |
| 6,214,008 B1 | 4/2001 | Illi |
| 6,214,796 B1 | 4/2001 | Finklestein |
| 6,221,861 B1 | 4/2001 | Seegmiller |
| 6,224,630 B1 | 5/2001 | Bao et al. |
| 6,225,340 B1 | 5/2001 | Wuthier et al. |
| 6,235,316 B1 | 5/2001 | Adkisson |
| 6,240,926 B1 | 6/2001 | Chin Gan et al. |
| 6,242,471 B1 | 6/2001 | Yasuma et al. |
| 6,245,108 B1 | 6/2001 | Biscup |
| 6,261,311 B1 | 7/2001 | Sharkey et al. |
| 6,261,586 B1 | 7/2001 | McKay |
| 6,264,695 B1 | 7/2001 | Stoy |
| 6,264,701 B1 | 7/2001 | Brekke |
| 6,265,632 B1 | 7/2001 | Yayon et al. |
| 6,274,322 B1 | 8/2001 | Curiel et al. |
| 6,283,980 B1 | 9/2001 | Vibe-Hansen et al. |
| 6,287,341 B1 | 9/2001 | Lee et al. |
| 6,290,715 B1 | 9/2001 | Sharkey et al. |
| 6,303,585 B1 | 10/2001 | Spiro et al. |
| 6,306,169 B1 | 10/2001 | Lee et al. |
| 6,306,177 B1 | 10/2001 | Felt et al. |
| 6,306,591 B1 | 10/2001 | Cockett et al. |
| 6,312,694 B1 | 11/2001 | Thorpe et al. |
| 6,312,952 B1 | 11/2001 | Hicks |
| 6,315,992 B1 | 11/2001 | Noh et al. |
| 6,326,029 B1 | 12/2001 | Geistlich et al. |
| 6,335,038 B1 | 1/2002 | Cavazza |
| 6,340,360 B1 | 1/2002 | Lyles et al. |
| 6,340,369 B1 | 1/2002 | Ferree |
| 6,342,219 B1 | 1/2002 | Thorpe et al. |
| 6,342,221 B1 | 1/2002 | Thorpe et al. |
| 6,344,058 B1 | 2/2002 | Ferree |
| 6,344,436 B1 | 2/2002 | Smith et al. |
| 6,346,086 B1 | 2/2002 | Maksem et al. |
| 6,346,519 B1 | 2/2002 | Petrus |
| 6,352,557 B1 | 3/2002 | Ferree |
| 6,352,558 B1 | 3/2002 | Spector |
| 6,365,405 B1 | 4/2002 | Salzmann et al. |
| 6,365,575 B1 | 4/2002 | Brigham et al. |
| 6,369,295 B1 | 4/2002 | Cheah et al. |
| 6,371,988 B1 | 4/2002 | Pafford et al. |
| 6,378,527 B1 | 4/2002 | Sohrabi et al. |
| 6,379,367 B1 | 4/2002 | Vibe-Hansen et al. |
| 6,391,905 B1 | 5/2002 | Yasuma et al. |
| 6,392,022 B1 | 5/2002 | Kato et al. |
| 6,398,816 B1 | 6/2002 | Breitbart et al. |
| 6,403,558 B1 | 6/2002 | Moses et al. |
| 6,406,693 B1 | 6/2002 | Thorpe et al. |
| 6,413,511 B1 | 7/2002 | Glorioso et al. |
| 6,416,758 B1 | 7/2002 | Thorpe et al. |
| 6,419,704 B1 | 7/2002 | Ferree |
| 6,425,920 B1 | 7/2002 | Hamada |
| 6,426,186 B1 | 7/2002 | Jones et al. |
| 6,428,576 B1 | 8/2002 | Haldimann |
| 6,429,013 B1 | 8/2002 | Halvorsen et al. |
| 6,432,436 B1 | 8/2002 | Gertzman et al. |
| 6,440,141 B1 | 8/2002 | Philippon |
| 6,440,444 B2 | 8/2002 | Boyce et al. |
| 6,443,988 B2 | 9/2002 | Felt et al. |
| 6,447,783 B1 | 9/2002 | Yayon |
| 6,447,809 B1 | 9/2002 | Krumhar et al. |
| 6,451,060 B2 | 9/2002 | Masuda et al. |
| 6,451,771 B1 | 9/2002 | Henderson et al. |
| 6,454,804 B1 | 9/2002 | Ferree |
| 6,454,811 B1 | 9/2002 | Sherwood et al. |
| 6,464,729 B1 | 10/2002 | Kandel |
| 6,464,983 B1 | 10/2002 | Grotendorst |
| 6,465,205 B2 | 10/2002 | Hicks, Jr. |
| 6,465,431 B1 | 10/2002 | Thorn et al. |
| 6,471,993 B1 | 10/2002 | Shastri et al. |
| 6,475,789 B1 | 11/2002 | Cech et al. |
| 6,479,469 B2 | 11/2002 | Anastassiades |
| 6,485,480 B1 | 11/2002 | Brewitt |
| 6,485,749 B1 | 11/2002 | Shalaby |
| 6,489,165 B2 | 12/2002 | Bhatnagar et al. |
| 6,489,351 B1 | 12/2002 | Yasuma et al. |
| 6,495,330 B1 | 12/2002 | Rademacher et al. |
| 6,500,854 B1 | 12/2002 | Kitamura et al. |
| 6,504,079 B2 | 1/2003 | Tucker et al. |
| 6,506,785 B2 | 1/2003 | Evans et al. |
| 6,511,511 B1 | 1/2003 | Slivka et al. |
| 6,511,800 B1 | 1/2003 | Singh |
| 6,517,568 B1 | 2/2003 | Sharkey et al. |
| 6,517,872 B1 | 2/2003 | Yayon et al. |
| 6,521,615 B2 | 2/2003 | Seegmiller |

(56) References Cited

U.S. PATENT DOCUMENTS

| | | |
|---|---|---|
| 6,524,583 B1 | 2/2003 | Thorpe et al. |
| 6,524,799 B1 | 2/2003 | Walker et al. |
| 6,528,052 B1 | 3/2003 | Smith et al. |
| 6,530,956 B1 | 3/2003 | Mansmann |
| 6,533,819 B1 | 3/2003 | Urry et al. |
| 6,545,124 B1 | 4/2003 | Bell et al. |
| 6,547,719 B1 | 4/2003 | Atala et al. |
| 6,547,810 B1 | 4/2003 | Sharkey et al. |
| 6,548,080 B1 | 4/2003 | Gertzman et al. |
| 6,552,066 B1 | 4/2003 | Sharpe et al. |
| 6,552,177 B2 | 4/2003 | Horowitz et al. |
| 6,555,650 B1 | 4/2003 | Lajoie et al. |
| 6,558,664 B1 | 5/2003 | Stringer et al. |
| 6,565,960 B2 | 5/2003 | Koob et al. |
| 6,569,172 B2 | 5/2003 | Asculai et al. |
| 6,569,442 B2 | 5/2003 | Gan et al. |
| 6,573,363 B1 | 6/2003 | Sheppard et al. |
| 6,576,668 B1 | 6/2003 | Aono et al. |
| 6,579,544 B1 | 6/2003 | Rosenberg et al. |
| 6,582,466 B1 | 6/2003 | Gauchet |
| 6,582,471 B1 | 6/2003 | Bittmann et al. |
| 6,582,960 B1 | 6/2003 | Martin et al. |
| 6,586,401 B1 | 7/2003 | Thorn et al. |
| 6,589,936 B1 | 7/2003 | Thorn et al. |
| 6,592,598 B2 | 7/2003 | Vibe-Hansen et al. |
| 6,592,599 B2 | 7/2003 | Vibe-Hansen et al. |
| 6,599,300 B2 | 7/2003 | Vibe-Hansen et al. |
| 6,599,301 B2 | 7/2003 | Vibe-Hansen et al. |
| 6,607,910 B1 | 8/2003 | Dimitrijevich et al. |
| 6,610,043 B1 | 8/2003 | Ingenito |
| 6,610,839 B1 | 8/2003 | Morin et al. |
| 6,613,044 B2 | 9/2003 | Carl |
| 6,616,698 B2 | 9/2003 | Scarborough |
| 6,617,110 B1 | 9/2003 | Cech et al. |
| 6,617,159 B1 | 9/2003 | Cancedda et al. |
| 6,617,161 B2 | 9/2003 | Luyten et al. |
| 6,620,203 B2 | 9/2003 | Atala |
| 6,623,963 B1 | 9/2003 | Muller et al. |
| 6,630,457 B1 | 10/2003 | Aeschlimann et al. |
| 6,637,437 B1 | 10/2003 | Hungerford et al. |
| 6,638,912 B2 | 10/2003 | Bhatnagar et al. |
| 6,645,247 B2 | 11/2003 | Ferree |
| 6,645,764 B1 | 11/2003 | Adkisson |
| 6,648,918 B2 | 11/2003 | Ferree |
| 6,648,919 B2 | 11/2003 | Ferree |
| 6,648,920 B2 | 11/2003 | Ferree |
| 6,653,283 B1 | 11/2003 | Moses et al. |
| 6,653,350 B1 | 11/2003 | Manning et al. |
| 6,656,925 B2 | 12/2003 | Petrus |
| 6,660,765 B2 | 12/2003 | Wuthier et al. |
| 6,662,805 B2 | 12/2003 | Frondoza et al. |
| 6,676,941 B2 | 1/2004 | Thorpe et al. |
| 6,676,969 B2 | 1/2004 | Geistlich et al. |
| 6,682,520 B2 | 1/2004 | Ingenito |
| 6,683,064 B2 | 1/2004 | Thompson et al. |
| 6,689,153 B1 | 2/2004 | Skiba |
| 6,689,747 B2 | 2/2004 | Filvaroff et al. |
| 6,696,073 B2 | 2/2004 | Boyce et al. |
| 6,696,410 B1 | 2/2004 | Lee et al. |
| 6,696,454 B2 | 2/2004 | Bar et al. |
| 6,696,578 B2 | 2/2004 | Gahunia et al. |
| 6,699,294 B2 | 3/2004 | Urry |
| 6,699,471 B2 | 3/2004 | Radice et al. |
| 6,703,020 B1 | 3/2004 | Thorpe et al. |
| 6,710,025 B1 | 3/2004 | Spector |
| 6,713,085 B2 | 3/2004 | Geistlich et al. |
| 6,716,628 B2 | 4/2004 | Kitamura et al. |
| 6,719,795 B1 | 4/2004 | Cornwall et al. |
| 6,719,797 B1 | 4/2004 | Ferree |
| 6,719,970 B1 | 4/2004 | Costantino et al. |
| 6,720,156 B2 | 4/2004 | Hutchins et al. |
| 6,723,335 B1 | 4/2004 | Moehlenbruck et al. |
| 6,723,535 B2 | 4/2004 | Ashkenazi et al. |
| 6,730,124 B2 | 5/2004 | Steiner |
| 6,730,314 B2 | 5/2004 | Jeshke et al. |
| 6,733,505 B2 | 5/2004 | Li |
| 6,750,028 B1 | 6/2004 | Geesin et al. |
| 6,752,834 B2 | 6/2004 | Geistlich et al. |
| 6,755,863 B2 | 6/2004 | Ferree |
| 6,761,739 B2 | 7/2004 | Shepard |
| 6,899,716 B2 | 5/2005 | Cragg et al. |
| 2001/0002401 A1 | 5/2001 | Evans et al. |
| 2001/0004710 A1 | 6/2001 | Felt et al. |
| 2001/0005592 A1 | 6/2001 | Bhatnagar et al. |
| 2001/0006634 A1 | 7/2001 | Zaleske et al. |
| 2001/0006948 A1 | 7/2001 | Kang et al. |
| 2001/0011100 A1 | 8/2001 | Wuthier et al. |
| 2001/0011131 A1 | 8/2001 | Luyten et al. |
| 2001/0012965 A1 | 8/2001 | Masuda et al. |
| 2001/0014475 A1 | 8/2001 | Frondoza et al. |
| 2001/0014831 A1 | 8/2001 | Scarborough |
| 2001/0016772 A1 | 8/2001 | Lee et al. |
| 2001/0016777 A1 | 8/2001 | Biscup |
| 2001/0020188 A1 | 9/2001 | Sander |
| 2001/0020476 A1 | 9/2001 | Gan et al. |
| 2001/0024823 A1 | 9/2001 | Vukicevic et al. |
| 2001/0031254 A1 | 10/2001 | Bianchi et al. |
| 2001/0031260 A1 | 10/2001 | Lee et al. |
| 2001/0031497 A1 | 10/2001 | Rolland et al. |
| 2001/0037017 A1 | 11/2001 | Luyten et al. |
| 2001/0039050 A1 | 11/2001 | Luyten et al. |
| 2001/0039261 A1 | 11/2001 | Finklestein |
| 2001/0043940 A1 | 11/2001 | Boyce et al. |
| 2001/0051799 A1 | 12/2001 | Ingenito |
| 2001/0051834 A1 | 12/2001 | Frondoza et al. |
| 2002/0005205 A1 | 1/2002 | Barry et al. |
| 2002/0009432 A1 | 1/2002 | Iwamoto et al. |
| 2002/0009761 A1 | 1/2002 | Hutchins et al. |
| 2002/0009806 A1 | 1/2002 | Hicks |
| 2002/0015719 A1 | 2/2002 | Kellner et al. |
| 2002/0022883 A1 | 2/2002 | Burg |
| 2002/0029083 A1 | 3/2002 | Zucherman et al. |
| 2002/0032488 A1 | 3/2002 | Brekke et al. |
| 2002/0037940 A1 | 3/2002 | Koob et al. |
| 2002/0038150 A1 | 3/2002 | Urry |
| 2002/0041900 A1 | 4/2002 | Olsen et al. |
| 2002/0045940 A1 | 4/2002 | Giannetti et al. |
| 2002/0045942 A1 | 4/2002 | Ham |
| 2002/0048595 A1 | 4/2002 | Geistlich et al. |
| 2002/0049242 A1 | 4/2002 | Yasuma et al. |
| 2002/0052044 A1 | 5/2002 | Jeschke et al. |
| 2002/0058614 A1 | 5/2002 | Filvaroff et al. |
| 2002/0058795 A1 | 5/2002 | Tagliaferri et al. |
| 2002/0061328 A1 | 5/2002 | Gertzman et al. |
| 2002/0076810 A1 | 6/2002 | Radice et al. |
| 2002/0081719 A1 | 6/2002 | Massaad et al. |
| 2002/0082623 A1 | 6/2002 | Osther et al. |
| 2002/0082698 A1 | 6/2002 | Parenteau et al. |
| 2002/0086333 A1 | 7/2002 | Gahunia et al. |
| 2002/0090391 A1 | 7/2002 | Geistlich et al. |
| 2002/0091444 A1 | 7/2002 | Yang |
| 2002/0091448 A1 | 7/2002 | Atala |
| 2002/0094754 A1 | 7/2002 | Stringer |
| 2002/0095144 A1 | 7/2002 | Carl |
| 2002/0098168 A1 | 7/2002 | Glorioso et al. |
| 2002/0103353 A1 | 8/2002 | Einat et al. |
| 2002/0106352 A1 | 8/2002 | Amir et al. |
| 2002/0106362 A1 | 8/2002 | Masuda et al. |
| 2002/0106393 A1 | 8/2002 | Bianchi et al. |
| 2002/0110544 A1 | 8/2002 | Goldberg et al. |
| 2002/0111695 A1 | 8/2002 | Kandel |
| 2002/0115060 A1 | 8/2002 | Ochi et al. |
| 2002/0115069 A1 | 8/2002 | Horowitz et al. |
| 2002/0115197 A1 | 8/2002 | Ochi et al. |
| 2002/0116069 A1 | 8/2002 | Urry |
| 2002/0119153 A1 | 8/2002 | Thorpe et al. |
| 2002/0119950 A1 | 8/2002 | Henderson et al. |
| 2002/0119952 A1 | 8/2002 | Petrus |
| 2002/0122790 A1 | 9/2002 | Hunziker |
| 2002/0123142 A1 | 9/2002 | Hungerford et al. |
| 2002/0123808 A1 | 9/2002 | Li |
| 2002/0128718 A1 | 9/2002 | Ferree |
| 2002/0133231 A1 | 9/2002 | Ferree |
| 2002/0133235 A1 | 9/2002 | Hungerford et al. |

(56) References Cited

U.S. PATENT DOCUMENTS

| | | |
|---|---|---|
| 2002/0136696 A1 | 9/2002 | Lee et al. |
| 2002/0142984 A1 | 10/2002 | Brigham et al. |
| 2002/0143400 A1 | 10/2002 | Biscup |
| 2002/0146398 A1 | 10/2002 | Vago et al. |
| 2002/0147329 A1* | 10/2002 | Luyten et al. ............... 536/23.5 |
| 2002/0151974 A1 | 10/2002 | Bonassar et al. |
| 2002/0151981 A1 | 10/2002 | Ferree |
| 2002/0156031 A1 | 10/2002 | Kazuhisa et al. |
| 2002/0156531 A1 | 10/2002 | Felt et al. |
| 2002/0156532 A1 | 10/2002 | Ferree |
| 2002/0156533 A1 | 10/2002 | Ferree |
| 2002/0159982 A1 | 10/2002 | Bonassar et al. |
| 2002/0160471 A1 | 10/2002 | Kisiday et al. |
| 2002/0160978 A1 | 10/2002 | Bar et al. |
| 2002/0165542 A1 | 11/2002 | Ferree |
| 2002/0168763 A1 | 11/2002 | Yan et al. |
| 2002/0169122 A1 | 11/2002 | Majumdar et al. |
| 2002/0169123 A1 | 11/2002 | El-Deiry et al. |
| 2002/0172935 A1 | 11/2002 | Drake et al. |
| 2002/0173456 A1 | 11/2002 | Smith et al. |
| 2002/0173481 A1 | 11/2002 | Ekman et al. |
| 2002/0173806 A1 | 11/2002 | Giannetti et al. |
| 2002/0173850 A1 | 11/2002 | Brodke et al. |
| 2002/0173851 A1 | 11/2002 | McKay |
| 2002/0176893 A1 | 11/2002 | Wironen et al. |
| 2002/0177224 A1 | 11/2002 | Madry et al. |
| 2002/0177903 A1 | 11/2002 | Geistlich et al. |
| 2002/0182261 A1 | 12/2002 | Dai et al. |
| 2002/0182728 A1 | 12/2002 | Ramiya et al. |
| 2002/0183258 A1 | 12/2002 | D'Lima et al. |
| 2002/0183829 A1 | 12/2002 | Dosher et al. |
| 2002/0183857 A1 | 12/2002 | Yang |
| 2002/0188353 A1 | 12/2002 | Philippon |
| 2002/0192263 A1 | 12/2002 | Merboth et al. |
| 2002/0192310 A1 | 12/2002 | Bland et al. |
| 2002/0192675 A1 | 12/2002 | Zauderer et al. |
| 2002/0198599 A1 | 12/2002 | Haldimann |
| 2003/0008911 A1 | 1/2003 | Evans et al. |
| 2003/0009023 A1 | 1/2003 | Luyten et al. |
| 2003/0009225 A1 | 1/2003 | Khandkar et al. |
| 2003/0009235 A1 | 1/2003 | Manrique et al. |
| 2003/0012765 A1 | 1/2003 | Thompson et al. |
| 2003/0022157 A1 | 1/2003 | Zauderer et al. |
| 2003/0026786 A1 | 2/2003 | Pittenger et al. |
| 2003/0026788 A1 | 2/2003 | Ferree |
| 2003/0027329 A1 | 2/2003 | Lee et al. |
| 2003/0027331 A1 | 2/2003 | Yan et al. |
| 2003/0036079 A1 | 2/2003 | Weindruch et al. |
| 2003/0036764 A1 | 2/2003 | Hamada |
| 2003/0039676 A1 | 2/2003 | Boyce et al. |
| 2003/0040113 A1 | 2/2003 | Muzuno et al. |
| 2003/0040800 A1 | 2/2003 | Li et al. |
| 2003/0045943 A1 | 3/2003 | Brekkee et al. |
| 2003/0050709 A1 | 3/2003 | Noth et al. |
| 2003/0054035 A1 | 3/2003 | Chu et al. |
| 2003/0059481 A1 | 3/2003 | Krumhar et al. |
| 2003/0060515 A1 | 3/2003 | Sharpe et al. |
| 2003/0064511 A1 | 4/2003 | Stringer et al. |
| 2003/0069639 A1 | 4/2003 | Sander et al. |
| 2003/0069641 A1 | 4/2003 | Reuter et al. |
| 2003/0074075 A1 | 4/2003 | Thomas et al. |
| 2003/0074076 A1 | 4/2003 | Ferree et al. |
| 2003/0077821 A1 | 4/2003 | Sah et al. |
| 2003/0082152 A1 | 5/2003 | Hedrick et al. |
| 2003/0082169 A1 | 5/2003 | Boyd |
| 2003/0082187 A1 | 5/2003 | Thorpe et al. |
| 2003/0083370 A1 | 5/2003 | Wuthier et al. |
| 2003/0091581 A1 | 5/2003 | Rademacher et al. |
| 2003/0095993 A1 | 5/2003 | Bentz et al. |
| 2003/0095994 A1 | 5/2003 | Geistlich et al. |
| 2003/0096015 A1 | 5/2003 | Kakar |
| 2003/0099620 A1 | 5/2003 | Zaleske et al. |
| 2003/0109038 A1 | 6/2003 | Thies |
| 2003/0114930 A1 | 6/2003 | Lim et al. |
| 2003/0118579 A1 | 6/2003 | Walker et al. |
| 2003/0120433 A1 | 6/2003 | Yokota et al. |
| 2003/0124132 A1 | 7/2003 | Gottstein et al. |
| 2003/0125748 A1 | 7/2003 | Li et al. |
| 2003/0129193 A1 | 7/2003 | Thorpe et al. |
| 2003/0129261 A1 | 7/2003 | Henderson et al. |
| 2003/0133915 A1 | 7/2003 | Smith et al. |
| 2003/0134266 A1 | 7/2003 | Drake et al. |
| 2003/0134790 A1 | 7/2003 | Langenfeld |
| 2003/0134792 A1 | 7/2003 | Pike et al. |
| 2003/0135209 A1 | 7/2003 | Seedhom et al. |
| 2003/0138473 A1 | 7/2003 | Koblish et al. |
| 2003/0138873 A1 | 7/2003 | Masuda et al. |
| 2003/0139374 A1 | 7/2003 | Thorpe et al. |
| 2003/0139591 A1 | 7/2003 | Luyten et al. |
| 2003/0144197 A1 | 7/2003 | Zheng et al. |
| 2003/0144203 A1 | 7/2003 | Bowen |
| 2003/0144743 A1 | 7/2003 | Edwards et al. |
| 2003/0148357 A1 | 8/2003 | Sheppard et al. |
| 2003/0152546 A1 | 8/2003 | Shalaby |
| 2003/0152556 A1 | 8/2003 | Lai et al. |
| 2003/0152558 A1 | 8/2003 | Luft et al. |
| 2003/0158245 A1 | 8/2003 | Yasuma et al. |
| 2003/0161817 A1 | 8/2003 | Young et al. |
| 2003/0165473 A1 | 9/2003 | Masuda et al. |
| 2003/0171810 A1 | 9/2003 | Steiner |
| 2003/0171811 A1 | 9/2003 | Steiner et al. |
| 2003/0175257 A1 | 9/2003 | Song et al. |
| 2003/0175276 A1 | 9/2003 | Thorpe et al. |
| 2003/0175410 A1 | 9/2003 | Campbell et al. |
| 2003/0175656 A1 | 9/2003 | Livne et al. |
| 2003/0175855 A1 | 9/2003 | Lavallie et al. |
| 2003/0175964 A1 | 9/2003 | Martin et al. |
| 2003/0176683 A1 | 9/2003 | Luyten et al. |
| 2003/0180263 A1 | 9/2003 | Geistlich |
| 2003/0180266 A1 | 9/2003 | McKay et al. |
| 2003/0180948 A1 | 9/2003 | Hutchins et al. |
| 2003/0181964 A1 | 9/2003 | Sharkey et al. |
| 2003/0185807 A1 | 10/2003 | Gazit et al. |
| 2003/0185809 A1 | 10/2003 | Song et al. |
| 2003/0185898 A1 | 10/2003 | Luyten et al. |
| 2003/0190381 A1 | 10/2003 | Blad et al. |
| 2003/0191061 A1 | 10/2003 | Brewitt |
| 2003/0191536 A1 | 10/2003 | Ferree |
| 2003/0194696 A1 | 10/2003 | Zauderer et al. |
| 2003/0194708 A1 | 10/2003 | Asundi et al. |
| 2003/0195256 A1 | 10/2003 | Singh |
| 2003/0195628 A1 | 10/2003 | Bao et al. |
| 2003/0195629 A1 | 10/2003 | Pafford et al. |
| 2003/0199443 A1 | 10/2003 | Deisher et al. |
| 2003/0203426 A1 | 10/2003 | Prayaga et al. |
| 2003/0204023 A1 | 10/2003 | Koob et al. |
| 2003/0204206 A1 | 10/2003 | Padua et al. |
| 2003/0208279 A1 | 11/2003 | Atala |
| 2003/0211075 A1 | 11/2003 | Thorpe et al. |
| 2003/0211076 A1 | 11/2003 | Li et al. |
| 2003/0211604 A1 | 11/2003 | Brown |
| 2003/0216721 A1 | 11/2003 | Diederich et al. |
| 2003/0220244 A1 | 11/2003 | Warzecha |
| 2003/0220283 A1 | 11/2003 | Glorioso et al. |
| 2003/0220649 A1 | 11/2003 | Bao et al. |
| 2003/0220692 A1 | 11/2003 | Shapiro et al. |
| 2003/0223537 A1 | 12/2003 | Puzas |
| 2003/0223965 A1 | 12/2003 | Song et al. |
| 2003/0224518 A1 | 12/2003 | Adkisson |
| 2003/0225021 A1 | 12/2003 | McKay et al. |
| 2003/0225331 A1 | 12/2003 | Diederich et al. |
| 2003/0229049 A1 | 12/2003 | Eek |
| 2003/0229400 A1 | 12/2003 | Masuda et al. |
| 2003/0232752 A1 | 12/2003 | Freeman et al. |
| 2003/0235564 A1 | 12/2003 | Doll et al. |
| 2003/0235589 A1 | 12/2003 | Demopulos et al. |
| 2003/0235813 A1 | 12/2003 | Luyten et al. |
| 2003/0236394 A1 | 12/2003 | Schwarz et al. |
| 2003/0236574 A1 | 12/2003 | Bittman et al. |
| 2004/0002761 A1 | 1/2004 | Rogers et al. |
| 2004/0006125 A1 | 1/2004 | Remington et al. |
| 2004/0009157 A1 | 1/2004 | Gazit et al. |
| 2004/0010251 A1 | 1/2004 | Pitaru et al. |
| 2004/0013663 A1 | 1/2004 | Choong-Chin et al. |

(56) References Cited

U.S. PATENT DOCUMENTS

| | | |
|---|---|---|
| 2004/0014205 A1 | 1/2004 | Banes |
| 2004/0018179 A1 | 1/2004 | Song et al. |
| 2004/0018188 A9 | 1/2004 | Walker et al. |
| 2004/0019381 A1 | 1/2004 | Pflueger |
| 2004/0023855 A1 | 2/2004 | John et al. |
| 2004/0024463 A1 | 2/2004 | Thomas et al. |
| 2004/0028662 A1 | 2/2004 | Bader |
| 2004/0030385 A1 | 2/2004 | Steiner |
| 2004/0030406 A1 | 2/2004 | Ochi et al. |
| 2004/0033214 A1 | 2/2004 | Young et al. |
| 2004/0033221 A1 | 2/2004 | Masuda et al. |
| 2004/0034427 A1 | 2/2004 | Goel et al. |
| 2004/0037812 A1 | 2/2004 | Giannetti et al. |
| 2004/0037819 A1 | 2/2004 | Pascher et al. |
| 2004/0037841 A1 | 2/2004 | Liew et al. |
| 2004/0038303 A1 | 2/2004 | Unger |
| 2004/0038868 A1 | 2/2004 | Ingenito |
| 2004/0044408 A1 | 3/2004 | Hungerford et al. |
| 2004/0044416 A1 | 3/2004 | Callegaro et al. |
| 2004/0047855 A1 | 3/2004 | Ingenito |
| 2004/0048370 A1 | 3/2004 | Dennis et al. |
| 2004/0048371 A1 | 3/2004 | Shimp |
| 2004/0049249 A1 | 3/2004 | Rubery et al. |
| 2004/0054414 A1 | 3/2004 | Trieu et al. |
| 2004/0058408 A1 | 3/2004 | Thomas et al. |
| 2004/0063619 A1 | 4/2004 | Carson et al. |
| 2004/0071786 A1 | 4/2004 | Grippi et al. |
| 2004/0072793 A1 | 4/2004 | Aeschlimann et al. |
| 2004/0073377 A1 | 4/2004 | Pittman et al. |
| 2004/0077592 A1 | 4/2004 | Thompson et al. |
| 2004/0078078 A1 | 4/2004 | Shepard |
| 2004/0078090 A1 | 4/2004 | Binette et al. |
| 2004/0083001 A1 | 4/2004 | Kandel |
| 2004/0088053 A1 | 5/2004 | Serhan et al. |
| 2004/0091540 A1 | 5/2004 | Desrosiers et al. |
| 2004/0092580 A1 | 5/2004 | Wuthier et al. |
| 2004/0093092 A1 | 5/2004 | Ferree |
| 2004/0096509 A1 | 5/2004 | Hutchens et al. |
| 2004/0101518 A1 | 5/2004 | Vacanti et al. |
| 2004/0101958 A1 | 5/2004 | Shimp |
| 2004/0102824 A1 | 5/2004 | Sharkey et al. |
| 2004/0102850 A1 | 5/2004 | Shepard |
| 2004/0106550 A1 | 6/2004 | Imaizumi |
| 2004/0109845 A1 | 6/2004 | Terkeltaub |
| 2004/0110209 A1 | 6/2004 | Yokota et al. |
| 2004/0111136 A1 | 6/2004 | Sharkey et al. |
| 2004/0111137 A1 | 6/2004 | Shankey et al. |
| 2004/0115172 A1 | 6/2004 | Bianchi et al. |
| 2004/0117015 A1 | 6/2004 | Biscup |
| 2004/0117019 A1 | 6/2004 | Trieu et al. |
| 2004/0117033 A1 | 6/2004 | Frondoza et al. |
| 2004/0121301 A1 | 6/2004 | Kato et al. |
| 2004/0122209 A1 | 6/2004 | Poole |
| 2004/0127396 A1 | 7/2004 | Dubois |
| 2004/0127963 A1 | 7/2004 | Uchida et al. |
| 2004/0127990 A1 | 7/2004 | Bartish et al. |
| 2004/0131610 A1 | 7/2004 | Thorpe et al. |
| 2004/0131621 A1 | 7/2004 | Thorpe et al. |
| 2004/0131622 A1 | 7/2004 | Thorpe et al. |
| 2004/0134502 A1 | 7/2004 | Mizuno et al. |
| 2004/0136968 A1 | 7/2004 | Zheng et al. |
| 2004/0136970 A1 | 7/2004 | Ellsworth |
| 2004/0137613 A1 | 7/2004 | Vacanti et al. |
| 2004/0138101 A1 | 7/2004 | Filvaroff et al. |
| 2004/0138128 A1 | 7/2004 | Lee et al. |
| 2004/0138204 A1 | 7/2004 | Harrington |
| 2004/0138285 A1 | 7/2004 | Okazaki |

FOREIGN PATENT DOCUMENTS

| | | |
|---|---|---|
| EP | 1091776 | 5/2004 |
| WO | WO9817209 A2 | 4/1998 |
| WO | WO9856433 | 12/1998 |
| WO | WO9961084 | 12/1999 |
| WO | WO0045747 | 8/2000 |
| WO | WO0108714 | 2/2001 |
| WO | WO0108715 | 2/2001 |
| WO | WO0145577 | 6/2001 |
| WO | WO0154629 | 8/2001 |
| WO | WO0187369 | 11/2001 |
| WO | WO 02/00142 A2 * | 1/2002 |
| WO | WO0200142 | 1/2002 |
| WO | WO0217825 | 3/2002 |
| WO | WO0222185 | 3/2002 |
| WO | WO02076336 | 8/2002 |
| WO | WO02087475 | 8/2002 |
| WO | WO02064181 | 10/2002 |
| WO | WO02062405 | 11/2002 |
| WO | WO03002021 | 1/2003 |
| WO | WO03037165 | 5/2003 |
| WO | WO03039328 | 5/2003 |
| WO | WO03049669 | 6/2003 |
| WO | WO03051239 | 6/2003 |
| WO | WO03105737 | 12/2003 |
| WO | WO2004024037 | 3/2004 |
| WO | WO2004026189 | 4/2004 |
| WO | WO2004037132 | 5/2004 |

OTHER PUBLICATIONS

Ganey et al., Eur. Spine J., 2002, 11(suppl. 2):S206-S214.*
Rahmat et al., J. Bone Joint Surg. Br. Apr. 2004, vol. 86-B, Suppl. 1, pp. 88.*
Brittberg et al., J. Bone Joint Surg. Am., Aug. 2003, vol. 85:109-115.*
Kuettner et al., J. Cell Bol., 1982, 93(3):743-750 (Abstract).*
Ganey et al., Spine, 2003, Dec. 1, vol. 28(23), 2609-2620.*
Peterson, Tech. Knee Surg., 2002, vol. 1(1):2-12.*

* cited by examiner

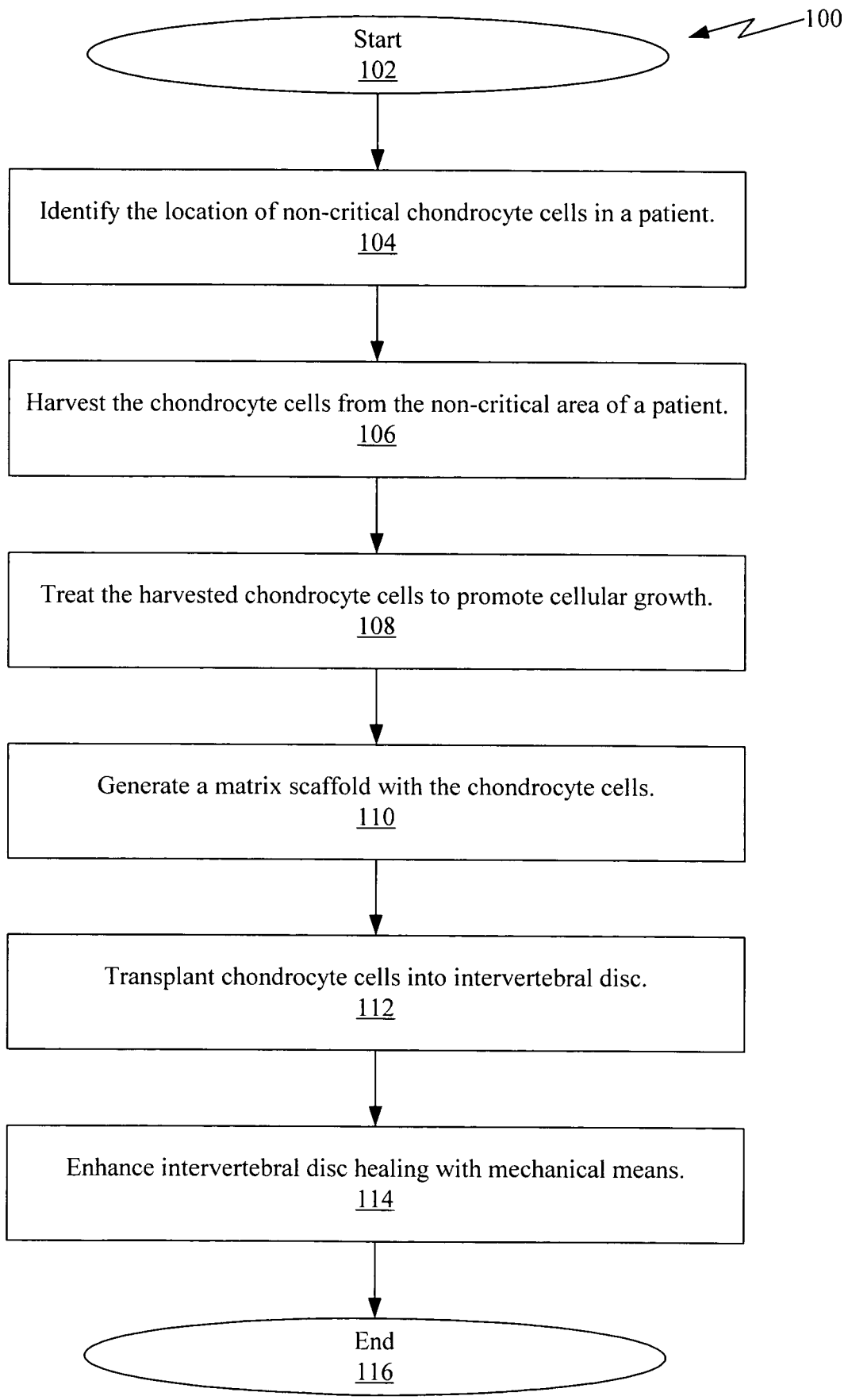

METHOD OF INTERVERTEBRAL DISC TREATMENT USING ARTICULAR CHONDROCYTE CELLS

BACKGROUND OF THE INVENTION

1. Field of the Invention

This invention relates generally to the treatment of diseased or traumatized intervertebral discs, and more particularly, to the use of engineered disc tissues in conjunction with such treatment.

2. Related Art

Intervertebral discs provide mobility and a cushion between the vertebrae. At the center of each disc is the nucleus pulposus, which in the adult human, is composed of cells and an insoluble extra-cellular matrix that is produced by the nucleus itself. The extracellular matrix is composed of collagen, proteoglycans, water, and noncollagenous proteins.

The cells of the nucleus pulposus have chondrocyte-like features. Blood vessels do not course into the nucleus pulposus. Rather, the cells of the nucleus pulposus of the adult human obtain nutrients and eliminate waste by diffusion through blood vessels in the endplates of the vertebrae adjacent to the disc.

The nucleus pulposus is surrounded by the annulus fibrosis, which is composed of cells (fibrocyte-like and chondrocyte-like), collagen fibers, and non-fibrillar extra-cellular matrix. The components of the annulus are arranged in 15-25 lamellae around the nucleus pulposus.

To date, the treatment of degenerative disc disease has relied for the most part on eliminating the defective disc or disc function. This may be accomplished by fusing the vertebra on either side of the disc. In terms of replacement, most prior-art techniques use synthetic materials to replace the entire disc or a portion thereof or harvested chondrocyte cells from a patient's own disk.

Unfortunately, disc replacement using synthetic materials does not restore normal disc shape, physiology, or mechanical properties. Synthetic disc replacements tend to wear out, resulting in premature failure. The problems associated with the wear of prosthetic hip and knees are well known to those skilled in orthopedic surgery. A more desirable approach for treating degenerative disc disease therefore lies in treatments that preserve disc function. If disc function could be restored with biologic replacement or augmentation, the risk of premature wear out would be minimized, if not eliminated.

A draw back with the known approach of harvesting chondrocyte cells from a disc for use in other disc is the additional risk inherent with medical procedures on a health disc. Even if cells are harvested from a diseased disc for later re-implantation in the same disc, this would necessitate multiple procedures on an already injured disc. Similarly, there are risks involved with rejection of cells that are harvested from cadavers or donors. Therefore, what is needed is a method and approach to heal an intervertebral disc with chondrocyte cells while reducing the medical risk associated with known approaches.

SUMMARY

An approach for treating a diseased or traumatized intervertebral discs using harvested, engineered tissue that is harvested from non-critical locations of a patient. Live, articular chondrocyte cells are harvested from a non-critical location of a patient, cultured, and transplanted while still viable into an affected intervertebral disc. The cultured cells may be collected and grown on an analogue of the extracellular matrix to yield an engineered disc tissue. Gene engineering approaches may be used to increase the efficient of the cultured cells. Collagen-glycosaminoglycans may provide the extracellular matrix, though alternative may be substituted.

Depending upon the target region of the recipient, the cells preferably differentiate into nucleus pulposus like cells, annulus fibrosis like cells, or both. To assist in differentiation, the nucleus pulposus like cells may be combined with various growth factors or type II collagen-glycosaminoglycans, and the annulus fibrosis like cells may be combined with type I collagen-glycosaminoglycans.

The cells or engineered tissues may be introduced using any surgical technique, including percutaneous or laparoscopic approaches. As one delivery mechanism, a passageway may be formed through the annulus fibrosis, with the cells or engineered disc tissue being introduced into the disc through the passageway. In particular, the engineered disc tissue may be morselized and injected into the disc with a needle and syringe or through a small cannula.

BRIEF DESCRIPTION OF THE FIGURES

The figure illustrates the method steps of an implementation of the invention with emphasis being placed upon illustrating the principles of the invention.

FIG. 1 illustrates the flow diagram of articular chondrocytes cell therapy.

DETAILED DESCRIPTION

Unlike known approaches that require autologous nucleus pulposus chondrocyte like cells obtained by aspiration or biopsy of discs of a patient, articular chondrocytes cells may be harvested from non-critical areas of a patient. Such non-critical areas may include knees or the talus area. Guidelines for tissue procurement including surgical techniques of removal are well described in the literature.

Turning to FIG. 1, a flow diagram 100 of articular chondrocytes cell therapy is illustrated. The flow diagram starts 102 with identifying the location of non-critical articular chondrocyte cells within a patient that may be harvested 104. The non-critical articular chondrocytes are harvested from the identified location 106. The harvested sterile nucleus pulposus from non-critical areas of a patient may be morselized and washed with phosphate buffered saline. The cells are released from the extracellular matrix with 0.2% clostridial collagenase (Worthington CLS II, 140 u/mg) and agitated. See Klagsburn, "Methods in Enzvmology, Vol. VII. The resulting suspension is filtered with a 153.mu.g nylon sieve (Tetko, Elmford, N.Y.).

The filtered solution is then centrifuged at 1800 rpm to remove the cells. The supernatant above the cells is removed with a micropipette until the cell concentration reaches $5.times.10.sup.7$ cells/cc. The harvested cells may be grown in a media, such as Hamm's F-12 culture media, 10% fetal calf serum, L-glutamine (292.mu.g/cc), penicillin (100 u/cc), streptomycin (100.mu.g/cc), and ascorbic acid (5.mu.g/cc) at 37 degrees C.

The harvested articular chondrocytes cells are then isolated and cultured using techniques that promote growth 108. A recent study highlighted the role played by the environment on the cells cultured. Chondrocytes grown in a matrix of type II collagen retained their chondrocyte features and synthesized materials for the extra-cellular matrix. Chnodrocytes grown in a matrix of type I collagen developed fibroblastic features and produced less material for the extra-cellular matrix. Cell culture with growth factors or with genes coding for growth factors including the BMP family may be used to expand the number of cells and turn on or enhance the mentioned desired traits of the Chondrocytes cells. The gene therapy using viral transduction using the BMP family is known in the art. Similarly, non-viral transduction gene therapy may be used to expand the number of cells or enhance cellular function.

The cultured cells may be directly transplanted in to a damaged or unhealthy disc. Another approach to transplanting the cultured cells includes the cultured cells being transferred and grown on an analogue of the extra-cellular matrix 110. Nucleus cells may be grown on a porous type II collagen-glycosaminoglycan matrix. Annulus fibrosis cells may be grown on a type I collagen-glycosaminoglycan matrix. Techniques to form the analogue extracellular matrices are known in the art. For example, Bovine type I collagen is precipitated from and acid dispersion with chondroitin-6-sulfate. The precipitated collagen is spread onto a flat surface or injected into a 3.8 mm (inside diameter) silicone tube. The collagen may then be cooled and freeze dried. The matrices can be cross-linked by dehydrothermal treatment, ultraviolet light, and using aldehydes or other crosslinking agents. The final matrix may be 95% porous. The average pore diameter is 30-120 um. A matrix using type II collagen may be similarly formed.

The cultured cells, preferably along with the reconstructed extra-cellular matrix, are transplanted by being injected into the affected disc 112. The extra-cellular matrix may be morselized to fit through a small cannula or needle. The fibers of the lamella alternate direction between layers. A blunt tipped needle or cannula could be forced through the annulus. Upon withdraw of the needle, after injecting the transplanted nucleus pulposus, the separated fibers of the lamella would return to their normal position, sealing the annulus. The cultured cells and engineered extra-cellular matrix of the annulus fibrosis may be injected into the annulus fibrosis. Those skilled in the art will realize the needle could be directed into the posterior or lateral portion of the disc percutaneously with fluoroscopic guidance and into the anterior portion of the disc laparoscopically. For example the transplanted nucleus is added to the patient's nucleus pulposus. Alternatively, the patient's nucleus may be removed with standard techniques (enzymatically (chymopapain) or with the aid of a laser, suction device, shaver, or other surgical instrument). If the nucleus is removed, the hole in the annulus should be small to facilitate closure at the end of the procedure.

Additional therapeutic substances may be added to the transplanted nucleus. For example, resorbable culture medium, tissue growth or differentiation factors (recombinant generated morphogenetic proteins, PDGF, TGF-.beta., EGF/TGF-.alpha., IGF-1, .beta.FGF), hydrogels, absorbable or nonresorbable synthetic or natural polymers (collagen, fibrin, polyglycolic acid, polylactic acid, polytetrafluoroethylene, etc.), antibiotics, anti-inflammatory medication, etc. could be beneficial. Mechanical means for off-loading or stabilizing the disc by providing support for the spine and/or disc during healing may also be employed to enhance the disc healing after articular chondrocytes transplantation has occurred 114. Such means may control loads and forces across the disc to promote growth of the cells and healing of the disc. Examples of mechanical means, my include braces, splints, pins, or other mechanical means that immobilize the treated level while off-loading or stabilizing one or more discs. The diagram is shown as stopping at step 116, but in practice the procedure may be conducted again on another disc or the same disc.

The foregoing description of an implementation has been presented for purposes of illustration and description. It is not exhaustive and does not limit the claimed inventions to the precise form disclosed. Modifications and variations are possible in light of the above description or may be acquired from practicing the invention. Note also that the implementation may vary between hospitals and medical professionals. The claims and their equivalents define the scope of the invention.

What is claimed is:

1. A method of treating a damaged intervertebral disc of a patient, comprising:
   identifying a location of a plurality of non-critical articular chondrocyte cells within the patient, where the plurality of non-critical articular chondrocyte cells are located in the patient's joints;
   harvesting a portion of the plurality of non-critical articular chondrocyte cells; and
   transplanting the portion of the plurality of non-critical articular chondrocyte cells that are isolated and absent their extra-cellular matrix into the damaged intervertebral disc.

2. The method of claim 1, further includes:
   culturing the portion of the plurality of non-critical articular chondrocyte cells after harvesting a portion of the plurality of non-critical articular chondrocyte cells, where the culturing results in chondrocytes cells.

3. The method of claim 2, where culturing includes:
   introducing a therapeutic substance into the portion of the plurality of non-critical articular chondrocyte cells.

4. The method of claim 3, where the therapeutic substance is recombinant generated morphogenetic proteins.

5. The method of claim 3, where the therapeutic substance is a nonresorbable polymer.

6. The method of claim 2, further includes:
   removing the cultured chondrocyte cells from any matrix produced during the culturing.

7. The method of claim 1, further including:
   Stabilizing the damaged intervertebral disc after transplanting the portion of the plurality of non-critical articular chondrocyte cells utilizing mechanical means comprising one or more of braces, splints, and pins.

* * * * *